United States Patent [19]

Shinoda et al.

[11] Patent Number: 5,194,473
[45] Date of Patent: Mar. 16, 1993

[54] MODIFIED POLYESTER COMPOSITION AND PREPARATION PROCESS AND USE THEREOF

[75] Inventors: Hosei Shinoda, Aichi; Masami Ohtaguro; Shigeru Iimuro, both of Nagoya, all of Japan

[73] Assignee: Mitsui Toatsu Chemicals, Inc., Tokyo, Japan

[21] Appl. No.: 525,729

[22] Filed: May 21, 1990

[30] Foreign Application Priority Data

| | | |
|---|---|---|
| May 26, 1989 [JP] | Japan | 1-131480 |
| Jun. 29, 1989 [JP] | Japan | 1-165400 |
| Jul. 3, 1989 [JP] | Japan | 1-169984 |

[51] Int. Cl.$^5$ ............................................. C08S 3/18
[52] U.S. Cl. ................................... 524/263; 524/265; 525/446; 528/26
[58] Field of Search ................. 525/446; 528/26; 524/265, 263

[56] References Cited

U.S. PATENT DOCUMENTS

| | | | |
|---|---|---|---|
| 4,613,641 | 9/1986 | Haubennestel et al. | 524/276 |
| 4,826,945 | 5/1989 | Cohn et al. | 525/450 |

FOREIGN PATENT DOCUMENTS

| | | |
|---|---|---|
| 165849 | 12/1985 | European Pat. Off. . |
| 299730 | 1/1989 | European Pat. Off. . |
| 389386 | 9/1990 | European Pat. Off. . |
| 56-45920 | 4/1981 | Japan . |
| 64-2383 | 1/1989 | Japan . |
| 993493 | 5/1965 | United Kingdom . |
| 8604072 | 11/1985 | World Int. Prop. O. . |

OTHER PUBLICATIONS

Polymer, 1979, vol. 20, Dec., "Biodegradable Polymers for Use in Surgery—Polyglycolic/Poly(actic acid) Homo— and Copolymers".

*Primary Examiner*—John C. Bleutge
*Assistant Examiner*—D. E. Aylward
*Attorney, Agent, or Firm*—Burns, Doane, Swecker & Mathis

[57] ABSTRACT

In preparing bioabsorbable polyesters containing glycolic acid unit and/or lactic acid unit by the polymerization of glycolide and/or lactide, compositions comprising polyester-silicone copolymers obtained by conducting polymerization in the presence of silicones and the effect of merely mixing the above bioabsorbable polyesters with certain kind of silicones upon the modification, thereby attaining flexibility in particular, of the bioabsorbable polyesters, are disclosed.

6 Claims, No Drawings

MODIFIED POLYESTER COMPOSITION AND PREPARATION PROCESS AND USE THEREOF

BACKGROUND OF THE INVENTION

1. Field of the Invention

The present invention relates to a bioabsorbable modified polyester composition mainly used for medical materials, a preparation process thereof and use of the composition.

The main ingredient of the modified polyester of the invention is a polyester containing at least glycolic acid recurring-units and/or lactic acid recurring units, or a polyester containing at least silicone modified glycolic acid recurring units and/or silicone modified lactic acid recurring units.

The present invention also relates to a modified polyester composition which can improve flexibility and softness of bioabsorbable polyester and extend its use for medical materials.

2. Description of the Prior Art

Polyesters represented by polylactic acid (hereinafter abbreviated as PLA), polyglycolic acid (hereinafter abbreviated as PGA) and glycolic acid/lactic acid copolymers (hereinafter abbreviated as PGLA) are interesting bioabsorbable materials. These materials are nonenzymatically hydrolyzed in vivo. The decomposition products, glycolic acid and lactic acid, are finally converted to carbon dioxide and water through a metabolic pathway, and are excreted externally.

For example, high molecular weight PGA is processed into a form of fiber and used for aseptic surgery materials such as sutures and gauzes.

PLA and PGLA are also excellent in processability and solubility in solvents and hence have already been used as the matrix of slow release medicines for intravenous injection by being processed into, for example, microspheres.

Japanese Patent Publication SHO 64-2383(1989) has disclosed that PGLA and PLA are processed into the form of film and used an adhesion inhibitor for curing diseases due to tissue adhesion.

The preparation of polyesters such as PGA, PLA and PGLA is well documented in the literature as exemplified by Polymer, Vol. 20, p1459(1979). The preparation is generally carried out by the ring-opening polymerization of glycolide and/or lactide which are dehydrated cyclic dimers of glycolic acid and latic acid.

A process for preparing polyesters by the dehydrating polycondensation of glycolic acid and/or lactic acid is also disclosed in, for example, Japanese Patent Laid-Open Publication SHO 56-45920(1981).

Polyesters such as PGA, PLA and PGLA are excellent in bioabsorbability and hence utilized in various medical materials.

Recently, it has been further desired to provide flexibility and softness to these polyesters.

For example, PLA and PGLA have a good film-forming ability and have been known to form a tough film by casting a solution of PLA and PGLA. However, these films are stiff and unsuitable for use in vivo, particularly for application to soft tissue.

According to the information of the present inventors, it has been confirmed that even the film of PGLA which is said to be the most flexible becomes stiff by completely removing the solvent remaining in the film after casting.

SUMMARY OF THE INVENTION

One object of the present invention is to provide a novel modified polyester composition and copolymer which are flexible, bioabsorbable and useful for medical materials, a preparation process for the composition and copolymer, and an intravitally implantable material prepared from the composition and copolymer.

As a result of an extensive investigation carried out in order to solve the above problems, the present inventors have unexpectedly found that, in the preparation of a bioabsorbable polyester composed of a glycolic acid unit and/or a lactic acid unit, a composition containing a polyester-silicone copolymer obtained by polymerizing glycolide or lactide in the presence of a silicone, or a mere admixture of the above bioabsorbable polyester with a certain kind of silicone is effective for the modification of the bioabsorbable polyester, particularly for the improvement of flexibility. Thus the present invention has been completed.

One aspect of the present invention is a polyester-silicone copolymer obtained by conducting the ring-opening polymerization of glycolide and/or lactide in the presence of a silicone having a hydroxyl group, a modified polyester composition containing the copolymer and a preparation process for the same.

Another aspect of the present invention is a modified polyester composition obtained by mixing a polyester containing at least a glycolic acid unit and/or a lactic acid unit with a polyether modified silicone, a copolymer thereof, and an intravitally implantable material composed of the composition or the copolymer.

The present invention provides a novel modified polyester composition, a copolymer and a mixture, any of which has a silicone chain in the polymeric structure. The novel and modified polyester composition, copolymer and the mixture thereof are excellent in flexibility, solubility and surface smoothness as compared with conventional bioabsorbable polyesters.

Additionally, the present invention provides a simple and reasonable process for preparing the above novel and modified polyester composition, the copolymer and the mixture. In the preparation process, the properties of the resulting modified polyester composition, the copolymer and the mixture, for example, hydrolyzability, solubility, and processability can be controlled by adjusting the amount and molecular weight of the silicone.

Further, the modified polyester composition and the copolymer which are provided by the invention are readily mixed with conventional PGA, PLA and PGLA, and hence can be utilized for the modification of these conventional polymers, particularly for the improvement of flexibility and solubility.

Further, the present invention provides a modified polyester composition obtained by uniformly mixing the bioabsorbable polyester with a polyether modified silicone.

The modified polyester composition of the present invention can provide medical materials which are soft and have good processability and high biocompatibility, for example, implanting materials such as artificial blood vessels, adhesion inhibiting materials, surgical sutures, coating materices for surgical sutures and matrices for slow release medicines.

DETAILED DESCRIPTION OF THE INVENTION

A detailed description will hereinafter be made on the polyester-silicone copolymer of the present invention, the modified polyester composition containing the copolymer, the process for the preparation of the copolymer and the composition, the modified polyester composition containing the silicone and the bioabsorbable polyester, and the intravitally implantable material composed thereof.

The principal ingredient of the copolymer and the composition in the present invention is the bioabsorbable polyester which is obtained by conducting the ring-opening polymerization of glycolide and/or lactide and has the glycolic acid unit and/or the lactic acid unit, or the polyester-silicone copolymer having the hydroxyl group containing silicone and the glycolic acid unit and/or the lactic acid unit as the constituting unit.

The glycolide and the lactide for use in the preparation of these ingredients are cyclic dimers, each of which is readily prepared by the dehydrating polymerization of glycolic acid and lactic acid, and successive dehydration, respectively.

Lactide includes D-lactide which is a cyclic dimer of D-lactic acid, L-lactide which is a cyclic dimer of L-lactic acid, meso lactide which is a cyclic dimer of D- and L-lactic acid, and DL-lactide which is a racemic mixture of D- and L-lactic acid. Any type of lactide can be used, in the present invention.

The polymerization in the invention can also be carried out in the presence of other lactones in addition to glycolide and/or lactide which are employed for the monomer. Exemplary lactones include β-propiolactone, β-butyrolactone, β-valerolactone, δ-valerolactone, ε-caprolactone, p-dioxanone and 3-methyl-1,4-dioxane-2,5-dione.

The silicone in the invention refers to a polyorganosiloxane having recurring structural units represented by the formula (VI):

wherein R is a hydrogen atom, halogen atom or an organic group; n is an integer of 1 to 4000; and each R may be the same or different.

The organic group represented by R in the formula (VI) includes, for example, a hydroxyl group, alkyl group, hydroxyalkyl group, aryl group, haloaryl group and polyoxyalkylene group. Exemplary polyorganosiloxanes include polydimethyl siloxane, polydiethyl siloxane, polyphenylmethyl siloxane, polychlorophenyl siloxane, polyfluoro siloxane and polyether modified polydimethyl siloxane.

Representative silicones of the invention have one or more terminal hydroxyl groups and are represented by the formula (I):

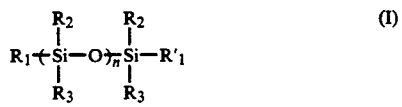

wherein $R_1$ and $R_1'$ are a hydrogen, an alkyl group, a hydrogen terminated polyoxyalkylene group having a polymerization degree of 200 or less, a hydroxyl group, a hydroxyalkyl group or a hydroxy terminated polyoxyalkylene group having a polymerization degree of 200 or less, and at least one of $R_1$ and $R_1'$ is a hydroxyl group or a hydroxy terminated group; $R_2$ and $R_3$ are alkyl groups, phenyl groups or halogen atoms, and may be the same or different; and n is an integer of 1 to 4000.

Another type of silicone of the invention has hydroxyl groups on the side chain of the polysiloxane and is represented by the formula (IV):

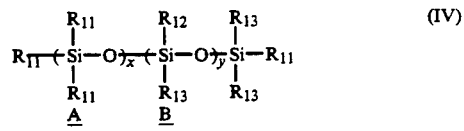

wherein $R_{11}$ is a hydrogen atom, halogen atom, alkyl group, or a phenyl group and may be the same or different; $R_{12}$ is a hydroxyl group, hydroxyalkyl group, hydroxy terminated polyoxyalkylene group having a polymerization degree of 2 to 200, or an alkyl group wherein one of its hydrogen atoms is substituted with a hydroxy terminated polyoxyalkylene group; $R_{13}$ is a hydrogen atom, halogen atom, alkyl group, phenyl group or the same group as $R_{12}$ and may be the same or different; X is an integer of 4000 or less, 0 inclusive; y is an integer of 1 to 4000; and recurring unit (A) and recurring unit (B) are arranged in random or in block.

No particular limitation is imposed upon the molecular weight of the silicone. The molecular weight (Mw) is preferably from 1,000 to 300,000 and more preferably from 10,000 to 100,000 with molecular weight less than 1,000, it is often difficult to give the polyester the desired flexibility. On the other hand, a molecular weight exceeding 300,000 leads to high viscosity of the silicone itself and difficulty in handling and also causes an unfavorable inhomogeneous polymerization reaction.

The polyester-silicone copolymer of the present invention and the modified polyester composition containing the copolymer can be prepared by the following process.

The amounts of the above glycolide and lactide for use in the preparation of the copolymer and the composition of the invention are determined depending upon the desired ratio of the lactic acid unit to the glycolic acid unit in the polyester. That is, the glycolide and lactide may be used singly or as a mixture in any arbitrary ratio.

More particularly, the amount of glycolide and/or lactide may be varied according to the object for the utilization of resulting modified polyester composition, polyester-silicone copolymer, or the composition containing the copolymer. That is, for example, when a polyester configuration in the structural units of the modified polyester or the polyester-silicone copolymer is polylactic acid or polyglycolic acid, lactide or glycolide, respectively, is used alone.

When said polyester is a copolymer of lactic acid and glycolic acid, the amount of lactic acid and glycolic acid can be determined depending upon the properties required for the resulting modified polyester or polyester-silicone copolymer.

Generally, known bioabsorbable polyesters obtained by the polymerization of glycolide and/or lactide are roughly divided into a lactic acid based polymer containing lactic acid as a principal component and a glycolic acid based polymer containing glycolic acid as a principal component. Glycolic acid based high molecular weight polymers are processed into fibers and used for sterilized surgery materials such as sutures and gauzes. Lactic acid-glycolic acid copolymers and lactic acid homopolymers are excellent in processability and solubility in solvents and are hence processed into pellets, needles, films and microspheres. These materials used for intravital implanting or as a matrix for slow release medicines for intravenous injection. High molecular weight lactic acid homopolymers, in particular, are processed into bars or plates and used for bioabsorbable bonesetting plates in the curing of fractures.

The modified polyester and the polyester-silicone copolymer of the invention exhibit softness as compared with unmodified bioabsorbable polyesters, have further improved applicability and are suitable for intravitally implanting materials. This characteristic is attained with modified polyesters prepared both by glycolide or lactide alone and with the combined use of glycolide and lactide. Consequently, the modified polyester composition and the polyester-silicone copolymer having softness can be obtained and employed for various medical materials having the above characteristics.

As mentioned above, the amount of glycolide and lactide can be determined depending upon the object for use.

The amount of silicone added in the polymerization of the above glycolide or lactide is in the range of preferably 0.05 to 50% by weight, more preferably 1 to 20% by weight.

Glycolide or lactide can be polymerized substantially in the absence of a catalyst. However, it is preferred to use a catalyst in order to obtain a high molecular weight polymer within a short time.

Various compounds which exhibit catalytic activity on the reaction can be used as the catalyst. Exemplary known catalysts include stannous octoate, tin tetrachloride, zinc chloride, titanium tetrachloride iron chloride, ether complex of boron trifluoride, aluminum chloride, antimony trifluoride, lead oxide and other compounds containing multivalent metals. Tin compounds and zinc compounds are preferably used. A particularly preferred tin compound is stannous octoate.

Polymerization may be carried out in the presence or absence of the catalyst. Bulk polymerization in a molten state is preferred.

When the silicone used in the polymerization has many hydroxyl groups in side chains or a number of oxyethylene groups at the end of polymer chain or in the side chains, the silicone is highly hydrophilic and has good compatibility with glycolide, lactide or polyester chain resulting from the polymerization. Accordingly, molten polymerization or bulk polymerization using such silicone progresses in a homogeneous system can be used.

However, other types of silicone are difficult to mix with monomers such as glycolide and lactide. Consequently, in the cases of molten polymerization or bulk polymerization in particular, it is desired to carry out vigorous stirring at the initial stage of polymerization to enlarge the contact surface of the silicone with monomers.

In the molten polymerization, the polymerization temperature may be in principle above the melting point of the monomer, i.e., glycolide or lactide. When solvents such as chloroform and dichloroethane are used, polymerization can be carried out at temperatures lower than the melting point. A temperature exceeding 250° C. is unfavorable because decomposition of the resulting polymer takes place.

The polyester-silicone copolymer of the invention and modofied polyester composition containing the copolymer can be prepared by the above preparation process.

According to the process of the invention, in the polymerization of glycolide or lactide in the presence of the silicone, the polymerization initiates at the terminal hydroxyl group of a silicone polymer chain and/or the side-chain hydroxyl group. As a result, the polymer contains glycolic acid chain or lactic acid chain combined with the end of silicone polymer chain and/or the side chain.

When the homopolymerization of glycolide or lactide or the copolymerization of glycolide and lactide is conducted in the presence of the silicone having at least one hydroxyl group at the end of silicone polymer chain, the block copolymer thus obtained has a configuration individually composed of PGA chain (chain of glycolic acid unit)-silicone, PLA chain (chain of lactic acid unit)-silicone, or PGLA chain (chain of glycolic acid and lactic acid units)-silicone.

When glycolide is initially polymerized in the presence of a silicone having hydroxyl groups on both ends of the silicone polymer chain and successively lactide is polymerized, PLA chain (A), PGA chain (B) and silicone chain (C) are combined and ABCBA type block copolymer can be obtained.

When the homopolymerization of glycolide or lactide or the copolymerization of glycolide and lactide is carried out in the presence of a silicone having hydroxyl groups in the side chains of the molecule, the graft copolymer thus obtained has a grafted chain individually composed of PGA, PLA or PGLA.

When glycolide is initially polymerized in the presence of a silicone having hydroxyl groups in the side chains and successively lactide is polymerized, the graft copolymer thus prepared can contain PGA-PLA block copolymer grafted on the side chains of the silicone.

Polyester chain (P) and silicone chain (S) in the block copolymer may be a PSP type or PS type. The polyester chain which constitutes chain P may be the homopolymer of glycolic acid or lactic acid or the block copolymer or random copolymer of these monomers. The structure depends upon the charging ratio and the charging procedures of glycolide and lactide.

The polyester-silicone copolymer of the invention is exemplified by the polyester-silicone copolymer represented by the following formula.

A polyester-silicone copolymer represented by the formula (II):

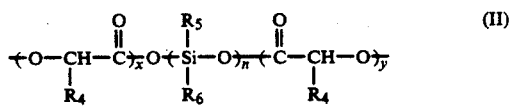

wherein $R_4$ is a hydrogen atom or a methyl group; $R_5$ and $R_6$ are alkyl groups, phenyl groups or halogen atoms, and may be the same or different; x and y are integers of 5,000 or less, 0 inclusive, and are not 0 at the same time; and n is an integer of 1 to 4000.

A polyester-silicone copolymer represented by the formula (III):

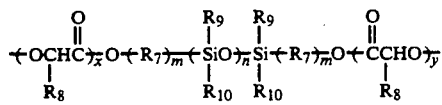

(III)

wherein $R_7$ is an alkylene group or an oxyalkylene group; $R_8$ is a hydrogen atom or a methyl group; $R_9$ and $R_{10}$ are alkyl groups, phenyl groups or halogen atoms and may be the same or different; x and y are integers of 5,000 or less, 0 inclusive and are not 0 at the same time; m is an integer of 200 or less, and 0 inclusive; and n is an integer of 1 to 4000.

A polyester-silicone copolymer represented by the formula (V):

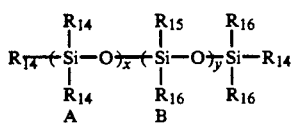

(V)

wherein $R_{14}$ is a hydrogen atom, halogen atom, group or a phenyl group, and may be the same or differentl $R_{15}$ is a polyester group or a -P-Q group wherein P is an oxyalkylene group, polyoxyalkylene group having a polymerization degree of 2 to 200, or a polyoxyalkylene group bonded to an alkyl group and Q is a polyester group and may be a homopolymer, block copolymer or a random copolymer of glycolic and lactic acid; $R_{16}$ is a hydrogen atom, halogen atom, alkyl group, phenyl group or the same group as $R_{15}$, and may be the same or different with each other; x is an integer of 4000 or less, 0 inclusive; y is an integer of 1 to 4,000; and recurring unit (A) and recurring unit (B) are arranged in random or in block.

No particular limitation is imposed upon the molecular weight(Mw) of the above copolymer. When the copolymer is used for a material which requires strength, a preferred molecular weight is 10,000 or more. However, when used as a matrix for slow release medicines, the molecular weight may be several hundred or more. A molecular weight exceeding a million unfavorably impairs processability or workability during polymerization.

The polyester-silicone copolymer is prepared by the polymerization of glycolide or lactide in the presence of the above silicone. The reaction product obtained is a mixture of the copolymer, silicone-uncombined polyester (hereinafter abbreviated as single polyester), polyester-uncombined silicone (hereinafter abbreviated as unreacted silicone), and unreacted glycolide and/or unreacted lactide.

The copolymer can be separated from the mixture. A preferred separation method is generally a conventional fractional precipitation method utilizing the difference in solubility. Unreacted glycolide or lactide can also be removed by heating under reduced pressure in the latter half of or after the polymerization reaction.

Confirmation of separation and purification results and characterization of the separated copolymer can be carried out by gel permeation chromatography (GPC), nuclear magnetic resonance (NMR), infrared adsorption spectroscopy (IR) and solubility test.

Exemplary modified polyester compositions of the invention include:

(1) a composition containing the above polyether-silicone copolymer as a required component, and (2) a composition containing the specific silicone compound and the polyester composed of at least glycolic acid units and/or lactic acid units as basic structural units.

The above composition is characterized by physically or chemically modifying the bioabsorbable polyester.

The modified polyester composition containing the polyester-silicone copolymer of the invention, i.e., the above polyester-silicone copolymer as a required component may be constituted by addition of other components so as to contain the isolated polyester-silicone copolymer as a component. The composition may also be constituted by the addition of the polyester-silicone copolymer mixture obtained in the above preparation process as is or after removal or incorporation of other components.

The reaction product obtained in the above process by conducting the ring-opening polymerization of glycolide and/or lactide in the presence of the silicone having hydroxyl groups in the structure thereof is a mixture containing the polyester-silicone copolymer represented by the above formula (II), formula (III) or formula (IV), single polyester without silicone, unreacted silicone without polyester, and unreacted glycolide and/or unreacted lactide.

In the composition, the proportion of the components is dependent upon various factors. For example, low purity of the monomers leads to a reduction in the polymerization degree and amount of the copolymer produced. A low concentration of hydroxyl groups in the silicone increases the molecular weight of the copolymer produced and the amount of single polyester is also liable to increase. The low concentration of hydroxyl groups also lowers the rate of polymerization and tends to increase the amount of the unreacted monomer. Further, a low compatibility of the silicone with the monomer used is liable to make the polymerization reaction inhomogeneous and leads to an increase in the amount of the unreacted silicone and single polyester.

No particular restriction is imposed upon the proportion of each component in the modified polyester composition of the invention. However, the amount of the unreacted monomer in particular is preferably 10% by weight or less in the composition in order to exhibit good mechanical strength of the modified polyester composition.

The modified polyester composition of the invention may also be prepared by removing unnecessary components from the mixture obtained by the above preparation process. Separation of the unnecessary components from the reaction mixture is generally conducted by conventional fractional precipitation methods utilizing the difference in solubility. Unreacted glycolide or lactide may also be eliminated by heating under reduced pressure in the latter half of or after polymerization.

Further, the modified polyester composition of the invention also includes a composition obtained by mixing the polyester-silicone copolymer or the above reaction mixture containing the copolymer with other bioabsorbable polyesters and/or other silicone compounds.

Generally, different kinds of polymers have poor compatibility and are difficult to mix. Consequently, bioabsorbable polyesters such as PGA, PLA and PGLA are very difficult to have flexibility by the addition of common silicones. On the other hand, the polyester-silicone copolymer of the invention has a conjugate-bond structure, has affinity for both polyester and silicone, and serves to increase compatibility. Consequently, an extremely uniform mixture can be obtained with other bioabsorbable polyesters or silicones.

The content of the polyester-silicone copolymer is preferably from 5 to 100% by weight in the composition. When the other bioabsorbable polyesters and/or other silicone compounds are added, the amounts of these materials are preferably from 0 to 95% by weight in the composition, from 0 to 20 times by weight of the polyester-silicone copolymer.

The modified polyester composition of the invention can be a mixture of the polyester composed of basic structural units containing at least glycolic acid units and/or lactic acid units and a specific silicone compound, i.e., polyether modified silicone.

A silicone having in the structure a polyether chain such as a polyoxyalkylene group, that is, a so-called polyether modified silicone exhibits good compatibility with the modified polyester composition containing the polyester-silicone copolymer of the invention and polyester-silicone copolymer itself. It has been unexpectedly found that the polyether modified silicone has also good compatibility with conventional polyesters such as PGA, PLA and PGLA and is hence effective for providing flexibility to the polyester.

The polyether modified silicone to be mixed with the polyester having at least glycolic acid units and/or lactic acid units is a polyorganosiloxane having as a substituent at least a hydroxyalkyl group or a polyoxyalkylene chain. A particularly preferred substituent is a polyoxyethylene chain having a polymerization degree in the range of 2 to 200. No particular limitation is placed upon the molecular weight. However, a molecular weight exceeding 3000 leads to high viscosity and it becomes difficult to obtain a uniform mixture.

High molecular compounds such as polyorganosiloxane which have Si-O bonds in its principal chain have a high bending ability of the chain and a weak intermolecular force, and hence have a low glass transition temperature and are very flexible.

However, as mentioned above, common polyorganosiloxane represented by polydimethylsiloxane, i.e., common silicone containing no polyoxyalkylene substituent is hydrophobic, almost insoluble in water and has poor compatibility with polyesters such as PGA, PLA and PGLA. When a common silicone is used for the plasticizer of the polyesters, phase separation takes place and expected flexibility cannot be obtained.

On the other hand, the polyether modified silicone used in the present invention is a polyorganosiloxane bonded with at least a hydroxyalkyl group or a polyoxyalkylene chain and hence exhibits hydrophilic properties. For example, polyether modified silicone having a structure in which about a half of methyl groups in polydimethylsiloxane is replaced with polyoxyethylene chain is completely soluble in water.

Further, the hydrophilic silicone has good compatibility with polyesters such as PGA, PLA and PGLA, and provides a uniformly blended mixture. Consequently, the resulting polyester composition has increased flexibility and surface smoothness as compared with the original polyester.

On preparing the composition of the invention, an admixture of the polyester and the polyether modified silicone may be carried out in the presence or absence of solvents. PLA and PGLA are soluble in an organic solvent such as chloroform and thus mixing can be readily carried out by previously dissolving one or both of the silicone and the polyester in the solvent.

PGA is difficultly soluble in organic solvents except a certain kind of solvent such as hexafluoroisopropanol. Consequently, it is favorable to mix by heat-melting above the melting point of about 225° C. However, heating above 250° C. is unfavorable because of decomposition of PGA.

The content of the polyether modified silicone is preferably in the range of 0.1 to 30% by weight in the composition.

Further, another aspect of the present invention is medical materials constituted with the modified polyester composition, polyester-silicone copolymer or the mixture thereof. More particularly, the medical materials include intervitally implantable materials such as artificial blood vessels and artificial skin, adhesion inhibiting materials, surgical sutures and coating materials thereof.

Silicone has already been used more than 30 years as a material for replacing soft tissue and is known to have biocompatibility. For example, silicone rubber obtained by curing silicone is utilized for artificial heart valves, artificial mamma, implanting material for retinal detachment surgery, artificial skin, artificial nose, artificial ear and artificial esophagus. The silicone used in the invention is an oil or gel at room temperature and physiologically almost inactive. For example, polydimethylsiloxane in particular has a $LD_{50}$ value, i.e., 50% lethal dose of 35 g/kg or more and corresponds to nontoxic in the toxicity classification. Consequently, the medical materials provided by the invention and constituted with the modified polyester composition polyester-silicone copolymer or the mixture thereof are suitable for biocompatible medical materials.

The modified polyester composition of the invention, polyester-silicone copolymer or the mixture thereof can be readily processed into fibers, films, plates, bars and other various shapes. Any of these processed materials are flexible and have increased solubility in organic solvents as compared with conventional polyesters such as PGA, PLA and PGLA. These effects result from the low glass transition temperature, small intermolecular forces and high flexibility of the silicone chain in the polyester composition, copolymer or the mixture.

The materials provided by the invention and constituted with the modified polyester composition, copolymer or the mixture can be used in a variety of applications by changing the composition of the silicone. That is, in the case where the silicone is very hydrophilic or the amount of the silicone is small although the silicone is slightly hydrophilic, the material containing said silicone can be used for bioabsorbable materials because the polyester chain can be hydrolyzed in vivo. For example, the material can be utilized for surgical sutures in the form of fibers, adhesion inhibiting materials after processing into films or sheets, bonesetting plates in the form of plates or bars and matrices of slow release medicines after mixing with medicines and successively processing into microspheres. Since the hydrophilic property of the material can be controlled by the variation of silicone composition, the rate of hydrolysis can be adjusted, which characteristic is very convenient for matrices of slow release medicines. On the other hand, in the case where the silicone is slightly hydrophilic and in a large amount, the hydrophilic property of the material itself is decreased and bioabsorbability is lost. Consequently, such material can be used for a non-absorbable and biocompatible material, for example, an implanting material for blood vessels. The material provided by the invention and constituted with the modified polyester composition, copolymer or the mixture can provide lubricity to the material surface as a result of the property of the silicone. Hence the material can enhance the ligating property (ease of knotting) of sutures when the material is employed for the coating of surgical sutures.

The present invention will hereinafter be illustrated further in detail with reference to examples.

Physical and chemical properties in the examples were measured by the following methods.

Polymerization Rate

After completing the polymerization reaction, the reaction mixture was dissolved in hexafluoroisopropanol (HFIP) or methylene chloride to make a solution having a known concentration. The amount of residual monomer was determined by gas chromatography and the polymerization rate was calculated.

Average Molecular Weight

Polymer was dissolved in HFIP and weight average molecular weight ($M_w$) and number average molecular weight (Mn) were measured by gel permeation chromatography (GPC).

Solution Viscosity

Polymer was dissolved in chloroform to prepare a solution having a concentration of 0.5 g/dl. Viscosity was measured at 25°±0.05° C. with an Ubbelohde viscosimeter. Solution viscosity $\eta$ was calculated from the following equation.

$$\eta = \log_e(T_1/T_0)/C$$

wherein
$T_0$ = Blank test time
$T_1$ = Test time
C = Concentration of solution (0.5 g/100 ml)

Tensile Strength Test

A film test piece having a width of 10 mm and a length of 50 mm was prepared. Tensile strength was measured with a chuck distance of 20 mm at a chuck separation rate of 50 mm/min.

Composition of Copolymer

Sample was dissolved in a deuterated chloroform/HFIP mixture (1/9) and H-NMR spectrum was measured with a 90 MHz NMR equipment. The mole ratio in the copolymer composition was calculated from the peak strength ratio based on methyl hydrogen in dimethylsiloxane, methylene hydrogen in glycolic acid unit, and methyl hydrogen in lactic acid unit, respectively.

Glass Transition Temperature (Tg)

Tg was measured with a differential scanning calorimeter at a temperature rise rate of 10° C./min.

Hydrolysis Test

A film specimen was immersed in a phosphoric acid buffer solution (pH 7.3) at 37° C. for a week. Evaluation was made by weight loss rate and Mw decrease rate of the film after immersion.

EXAMPLES 1-5

In a glass polymerization tube, 6.11 g of lactide and 4.36 g of glycolide were charged and various silicones illustrated in Table 1 were added in a prescribed amount, respectively. The silicones added were a silicone having hydroxyl groups at both ends (t-OH type), having hydroxyalkyl groups at both ends (t-ROH type), having a hydroxy terminated polyether in the side chain (b-ROH type i.e., polyether modified silicone, OH equivalent of 800), and having a hydroxyl group in the side chain (b-OH type, OH equivalent of 200). As a catalyst, 0.1 ml of stannous octoate solution in toluene (64.8 mg/10 ml) was added. The polymerization tube was fitted with a degassing cock, dried by deairing for several hours and melt-sealed under vacuum. Reaction was conducted in an oil bath at 180° C. for 18 hours. Reaction mixtures obtained are illustrated in Table 1.

The reaction product contained a small amount of residual monomers and illustrated that polymerization progressed at a high rate. GPC measurement revealed that most of the reaction product was polymers having distinctly higher molecular weights than the silicone used and also confirmed that almost no unreacted silicone remained.

The polymer was dissolved in methylene chloride, cast on a Teflon plate and the solvent was evaporated at room temperature to form a film. The film was further dried at 50° C. for 24 hours under a reduced pressure of 3 mm Hg. Complete removal of the residual solvent in the film was confirmed by IR measurement.

Results of tensile strength test at 37° C. are illustrated in Table 2. Any of these films had very low tensile Young's modulus and high elongation and were soft.

Any of these polymers were hydrolyzed in an environment similar to in vivo, and the weight and the molecular weight decreased.

That is, these films were suited for applying to intravital tissue in the form of, for example, implanting material or adhesion inhibiting material.

COMPARATIVE EXAMPLE 1

Polymerization was conducted by the same procedures as carried out in Examples 1-5 except that silicones having hydroxyl groups was not added. The polymerization rate was lower than that of Examples 1-5 under the same conditions. The compositions obtained were difficulty soluble in methylene chloride and chloroform and thus were dissolved in HFIP to cast films. The films obtained were stiff. Table 2 illustrates results on tensile strength tests. These films had tensile Young's modulus about 2 orders higher than those of Examples 1-5. Results on the hydrolysis tests are also illustrated in Table 2.

COMPARATIVE EXAMPLE 2

Polymerization was carried out by the same procedures as conducted in Examples 1-5 except that 0.40% of a 90% aqueous lactic acid solution was used in place of the silicones having hydroxyl groups in the side chain. The polymerization rates of glycolide and lactide were 99.4% and 98.9%, respectively. Mw calculated from GPC was 52000.

Stiff films were obtained by the same procedures as carried out in Example 1. Results on tensile strength tests at 37° C. are illustrated in Table 2. These films had Young's modulus 2 orders higher than that of Example 1. Results on hydrolysis tests are also illustrated in Table 2.

EXAMPLES 6-8 AND COMPARATIVE EXAMPLE 3

To a glass polymerization tube, 5.76 g of L-lactide and a prescribed amount(Table 3) of polydimethylsiloxane (t-OH type, Mw 8900) were charged and 0.1 ml of a stannous octoate solution (32.4 mg/10 ml) was added as a catalyst. The tube was fitted with a deaeration tube, dried by degassing for several hours and melt-sealed under vacuum. Polymerization was carried out by dipping the tube in an oil bath at 180° C. for 18 hours.

After finishing the polymerization, the reaction mixture was dissolved in 100 ml of methylene chloride and poured into about 1000 ml of methanol. The resulting precipitate was filtered and dried. Unreacted monomer and low molecular weight single polyester were removed into the filtrate in this step. The resulting methanol insoluble polymer was dissolved again in methylene chloride and the solution thus obtained was successively poured into n-hexane. The resulting precipitate was filtered and dried to obtain polymer. The unreacted silicone was soluble in n-hexane, and hence removed into the filtrate in this step.

The polymer obtained had only one peak in the GPC curve. NMR spectrum of the isolated polymer clearly exhibited methyl hydrogen peak (1.6 ppm) and methylene hydrogen peak (5.1 ppm) which resulted from PLA and additionally methyl hydrogen peak (0.08 ppm) resulting from silicone. These results proved that the polymer obtained had a bonded structure of polyester chain and silicone chain. Copolymer compositions calculated from peak strength ratio are illustrated in Table 3.

The polymer was dissolved in chloroform and cast on a Teflon plate. Solvent was evaporated at room temperature and completely removed by further standing under reduced pressure. A transparent film was obtained. Results on tensile strength test are illustrated in Table 4. The films obtained in Example 6-8 had definitely lower tensile Young's modulus and were softer than the film obtained in Comparative Example 3.

EXAMPLES 9-11 AND COMPARATIVE EXAMPLE 4

To a glass polymerization tube, prescribed amounts(Table 5) of DL-lactide, glycolide and polydimethylsiloxane (average molecular weight 8900, hydroxyl groups at both ends) were charged and 0.1 ml of a stannous octoate solution in toluene (64.8 mg/10 ml) was added as a catalyst. The tube was fitted with a degassing tube, dried by deaerating for several hours and melt-sealed under vacuum. Polymerization was carried out by dipping the sealed tube in an oil bath at 180° C. for 18 hours.

After finishing the polymerization, the reaction mixture is dissolved in 100 ml of methylene chloride and poured into about 1000 ml of n-hexane. The precipitate formed was filtered, dried and dissolved again in methylene chloride. The resulting solution was successively poured into methanol. The precipitate formed was filtered and dried to obtain polymer.

The polymers obtained in Examples 9-10 had lower glass transition temperatures (Tg) as compared with the polymer obtained in Comparative Example 4 and hence flexibility was clearly increased. Tg of polymers obtained in Examples 10 and 11 in particular, was close to body temperature (37° C.), and hence, the cast film was converted to very soft film while handling the film. These films were suitable for applying to soft tissue as implanting materials or adhesion inhibiting materials.

EXAMPLE 12

Into a test tube, 1 g of the composition obtained in Example 3 and 1 g of the polymer obtained in Comparative Example 2 were charged and stirred for 5 minutes under a nitrogen stream in an oil bath 200° C. A uniform mixture thus obtianed was dissolved in chloroform and cast on a Teflon plate to form a film of 84 μm in thickness. The film had a tensile Young's modulus of 5.5 kgf/mm$^2$ and an elongation of 520%.

EXAMPLE 13

Into a test tube, 1 g of the polymer obtained in Example 8 and 1 g of the polymer PLA obtained in Comparative Example 3 were charged and stirred for 5 minutes under a nitrogen stream in an oil bath of 200° C. A uniform mixture was obtained.

EXAMPLE 14

One part by weight of a 10% methylene chloride solution of the polymer obtained in Example 2 was mixed with 10 parts by weight of a 10% methylene chloride solution of polydimethylsiloxane having methyl groups at both ends (—CH$_3$ type, Mw 8000). The resultant dispersion maintained stable state for about several hours and thereafter separated into two transparent layers.

The dispersion was cast on a Teflon plate. The film thus obtained(blended film) was translucent and softer than the film obtained in Example 2 as illustrated in Table 6. The film was hydrolyzed under an environment similar to in vivo, and weight loss and molecular weight decrease were observed.

EXAMPLE 15

Into a test tube, 1 g of copolymer obtained in Example 8 and and 0.2 g of polydimethylsiloxane having methyl groups at both ends were charged, and stirred for 5 minutes under a nitrogen stream in an oil bath at 200° C. to obtain an uniform mixture.

EXAMPLES 16-18

A 10% methylene chloride solution of the copolymer PGLA obtained in Comparative Example 2 was mixed with silicone having hydroxyethyl groups at both ends (t-ROH type) or silicone having polyoxyethylene chains in the side chains (b-ROH type) in an amount of 20 parts by weight or 10 parts by weight, respectively, per 100 parts of the polyester. The mixtures were individually cast on a Teflon plate, and the solvent was evaporated at room temperature to form films. Residual solvent in the films was completely removed by drying at 50° C. for 24 hours under reduced pressure of 3 mm Hg.

Table 6 illustrates results on the tensile test of films.

Any film had very low Young's modulus and high elongation and was soft. These films were hydrolyzed under an environment similar to in vivo, and decrease in weight and molecular weight was observed. These films were suitable for applying to soft tissue as implanting materials or adhesion inhibiting materials.

EXAMPLE 19

A 10% methylene chloride solution of the copolymer obtained in Example 3 was mixed with a 10% methylene chloride solution of polyether modified b-ROH type silicone (OH equivalent 800) in an amount of 10 parts by weight per part by weight of the copolymer. The mixture obtained was uniform and transparent. The mixture was cast on a Teflon plate and dried to form a film. The film thus obtained (blended film) was uniform, transparent and softer than the film obtained in Example 3 as illustrated in Table 6.

These films were hydrolyzed under an environment similar to in vivo, and weight and molecular weight of the films decreased.

EXAMPLE 20

Chloroform solutions each containing 5% of polymers obtained in Example 1 and Example 8 were individually charged in test tubes of 1 cm in diameter and solvent removed with rotation at a temperature from room temperature to 50° C. under reduced pressure of 5 mm Hg or less. Thus, the internal surface of the test tubes was uniformly coated with the polymer. Directly after blood collection, 1 ml of whole human blood was charged to the test tube and maintained at 37° C. After standing for 5 minutes, the test tubes were tilted at an angle of 45 degrees every minute and whether the blood flowed or not was observed. As a result of conducting the test 10 times, the period until stopping the flowability of the blood was from 2 to 4 times longer in the coated tube than in an uncoated tube.

TABLE 1

|  | DL-Lactide (g) | Glycolide (g) | Silicone[*1] Type | Mw | (g) | Catalyst[*2] (mg) | Reaction Temperature (°C.) | Reaction time (hr) | Polymerization rate (%) Lactide | Glycolide | Mw |
|---|---|---|---|---|---|---|---|---|---|---|---|
| Example | | | | | | | | | | | |
| 1 | 6.11 | 4.36 | t-OH | 41300 | 1.186 | 0.648 | 180 | 18 | 96.1 | 99.8 | 59000 |
| 2 | 6.11 | 4.36 | t-ROH | 11100 | 1.186 | 0.648 | 180 | 18 | 97.5 | 99.4 | 29000 |
| 3 | 6.11 | 4.36 | b-ROH | 11200 | 1.186 | 0.648 | 180 | 18 | 95.8 | 98.9 | 42000 |
| 4 | 6.11 | 4.36 | b-ROH | 11200 | 0.593 | 0.648 | 180 | 18 | 98.1 | 99.5 | 65000 |
| 5 | 6.11 | 4.36 | b-OH | 9900 | 1.186 | 0.648 | 180 | 18 | 95.8 | 97.9 | 38000 |
| Comparat. Example | | | | | | | | | | | |
| 1 | 6.11 | 4.36 | | | 0 | 0.648 | 180 | 18 | 91.4 | 93.9 | 80000 |
| 2 | 6.11 | 4.36 | | | 0[*3] | 0.648 | 180 | 18 | 98.9 | 99.4 | 52000 |

[*1] t-OH:

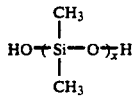

t-ROH:

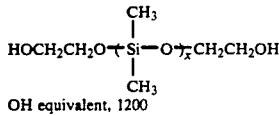

OH equivalent, 1200 b-ROH:

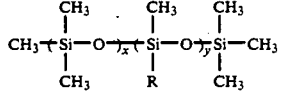

OH equivalent, 800; R: $-(CH_2)_3(O-CH_2CH_2)_n-OH$ b-OH:

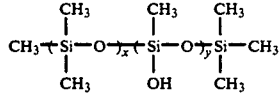

OH equivalent, 200

[*2] Stannous octoate
[*3] Aqueous 90% lactic acid solution, 0.04% addition

TABLE 2

|  | Film thickness (μm) | Young's modulus (Kgf/mm²) | Elongation (%) | Hydrolysis, 1 week weight loss (%) | Mw decrease (%) |
|---|---|---|---|---|---|
| Example | | | | | |
| 1 | 88 | 0.3 | 700 | 13.2 | 64 |
| 2 | 93 | 4.7 | 660 | 3.2 | 31 |
| 3 | 90 | 0.8 | 780 | 4.9 | 37 |
| 4 | 88 | 2.1 | 690 | 4.4 | 47 |
| 5 | 85 | 8.9 | 400 | 3.7 | 40 |
| Comparat. Example | | | | | |
| 1 | 89 | 103 | 70 | 8.1 | 49 |
| 2 | 48 | 121 | 25 | 3.2 | 67 |

TABLE 3

|  | L-Lactide (g) | Silicone (mg) | Catalyst[*2] (mg) | Reaction Temperature (°C.) | Time (hr) | Polymer yield[*3] (%) | η | Mw | Mw/Mn | Copolymer composition Siloxane/Lactic acid[*4] | Tg (°C.) |
|---|---|---|---|---|---|---|---|---|---|---|---|
| Example | | | | | | | | | | | |
| 6 | 5.76 | 5.8 | 0.324 | 180 | 18 | 91.4 | 2.56 | 208000 | 2.7 | 0.2/99.9 | 63 |
| 7 | 5.76 | 58.0 | 0.324 | 180 | 18 | 84.5 | 1.36 | 155000 | 3.3 | 0.0/99.1 | 58 |

TABLE 3-continued

| | L-Lactide (g) | Silicone (mg) | Catalyst*2 (mg) | Reaction Temperature (°C.) | Time (hr) | Polymer yield*3 (%) | η | Mw | Mw/Mn | Copolymer composition Siloxane/ Lactic acid*4 | Tg (°C.) |
|---|---|---|---|---|---|---|---|---|---|---|---|
| 8 | 5.76 | 580.0 | 0.324 | 180 | 18 | 88.6 | 0.78 | 78800 | 3.8 | 3.6/96.7 | 58 |
| Compare. Example 3 | 6.11 | 0 | 0.324 | 180 | 18 | 88.7 | 2.15 | 244000 | 2.4 | 0/100 | 63 |

*1Polydimethylsiloxane (t-OH type, Mw = 8900)
*2Stannous octoate
*3Methanol and hexane insoluble portion
*4Mole ratio

TABLE 4

| | Average film thickness (μm) | Young's modulus (Kgf/mm2) | Elongation (%) |
|---|---|---|---|
| Example | | | |
| 6 | 33 | 64 | 150 |
| 7 | 38 | 29 | 465 |
| 8 | 30 | 87 | 19 |
| Comparat. Example 3 | 32 | 188 | 3 |

TABLE 5

| | DL-Lactide (g) | Glycolide (g) | Silicone*1 (g) | Catalyst*2 (mg) | Reaction Temperature (°C.) | time (hr) | Polymer yield*3 (%) | η | Copolymer composition*4 Siloxane/ Lactic acid/ glycolic acid | Tg (°C.) |
|---|---|---|---|---|---|---|---|---|---|---|
| Example | | | | | | | | | | |
| 9 | 6.11 | 4.36 | 0.119 | 0.648 | 180 | 18 | 80.5 | 1.32 | 0.5/51/7/47.8 | 48 |
| 10 | 6.11 | 4.36 | 0.593 | 0.648 | 180 | 18 | 70.0 | 0.82 | 1.4/50.5/48.1 | 46 |
| 11 | 6.11 | 4.36 | 1.186 | 0.648 | 180 | 18 | 61.4 | 0.59 | 2.3/50/4/47.3 | 37 |
| Comparat. Example 4 | 6.11 | 4.36 | 0 | 0.648 | 180 | 18 | 81.4 | 1.50 | 0/52.0/18.0 | 55 |

*1Polydimethylsiloxane (t-OH type, Mw = 8900)
*2Stannous octoate
*3Methanol and hexane insoluble portion
*4Mole ratio

TABLE 6

| | Blended silicone (wt. part) | Total silicone content in film (wt. part) | Average film thickness (μm) | Young's modulus (Kgf/mm2) | Elongation (%) | Hydrolysis 1 week Weight loss (%) | Mw decrease (%) |
|---|---|---|---|---|---|---|---|
| Example | | | | | | | |
| 14 | —CH3  10 | 21 | 89 | 0.6 | 800 | 4.3 | 21 |
| 16 | t-ROH  20 | 20 | 87 | 6.9 | 610 | 10.5 | 58 |
| 17 | b-ROH  20 | 20 | 77 | 8.4 | 550 | 14.0 | 58 |
| 18 | b-ROH  10 | 10 | 79 | 12.2 | 350 | 8.6 | 63 |
| 19 | b-ROH  10 | 21 | 93 | 0.3 | 820 | 8.8 | 26 |

What is claimed is:

1. A bioabsorbable polyester composition obtaining by mixing a polyester containing at least a glycolic acid unit and/or a lactic acid unit with a polyether modified siloxane represented by the formula (I)

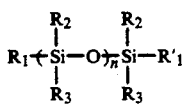

wherein $R_1$ and $R_1'$ are a hydrogen, an alkyl group, a hydrogen terminated polyoxyalkylene group having a polymerization degree of 200 or less, a hydroxyl group, a hydroxyalkyl group or a hydroxy terminated poly- oxyalkylene group having a polymerization degree of 200 or less, and at least one of $R_1$ and $R_1'$ is a hydroxy terminated polyoxyalkylene group having a polymerization degree of 200 or less, or a hydroxy terminated polyoxyalkylene group having a polymerization degree of 200 or less; $R_2$ and $R_3$ are alkyl groups, phenyl groups or halogen atoms, and may be the same or different; and n is an integer of 1 to 4000, wherein the content of the polyether modified siloxane is in the range of 0.1 to 30% by weight in the composition.

2. The bioabsorbable polyester composition of claim 1 wherein the polyester is polyglycolic acid, polylactic acid or glycolic-lactic acid copolymer obtained by conducting ring-opening polymerization of glycolide and-/or lactide in the presence of a silicone having a hydroxyl group.

3. An intravitally implanting material comprising a bioabsorbable polyester composition of claim 1.

4. A bioabsorbable polyester composition obtaining by mixing a polyester containing at least a glycolic acid unit and/or a lactic acid unit with a polyether modified siloxane represented by the formula (IV)

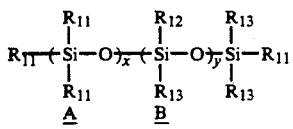

wherein $R_{11}$ is a hydrogen atom, a halogen atom, alkyl group, or a phenyl group and may be the same or different; $R_{12}$ is a hydroxy terminated polyoxyalkylene group having a polymerization degree of 2 to 200, or an alkyl group wherein one of its hydrogen atoms is substituted with a hydroxy terminated polyoxyalkylene group; $R_{13}$ is a hydrogen atom, halogen atom, alkyl group, phenyl group or the same group as $R_{12}$ and may be the same or different; X is an integer of 4000 or less, 0 inclusive; y is an integer of 1 to 4000; and recurring unit (A) and recurring unit (B) are arranged in random or in block, wherein the content of the polyether modified siloxane is in the range of 0.1 to 30% by weight in the composition.

5. The bioabsorbable polyester composition of claim 4 wherein the polyester is polyglycolic acid, polylactic acid or glycolic-lactic acid copolymer obtained by conducting ring-opening polymerization of glycolide and/or lactide in the presence of a silicone having a hydroxyl group.

6. An intravitally implanting material comprising a bioabsorbable polyester composition of claim 4.

* * * * *

UNITED STATES PATENT AND TRADEMARK OFFICE
CERTIFICATE OF CORRECTION

PATENT NO. :   5,194,473
DATED      :   March 16, 1993
INVENTOR(S) :  Shinoda et al.

It is certified that error appears in the above-identified patent and that said Letters Patent is hereby corrected as shown below:

Column 17, line 55, amend "obtaining" to --obtained--.

Column 18, line 61, delete "silicone" and insert therefor --siloxane--.

Column 18, line 65, amend "obtaining" to --obtained--.

Column 20, line 11, delete "silicone" and insert therefor --siloxane--.

Signed and Sealed this

Eighth Day of February, 1994

Attest:

BRUCE LEHMAN

*Attesting Officer*   *Commissioner of Patents and Trademarks*